(12) United States Patent
Liang

(10) Patent No.: US 12,036,260 B1
(45) Date of Patent: Jul. 16, 2024

(54) COMPOSITION FOR RELIEVING SLEEP DISORDER AND ITS APPLICATION METHOD THEREOF

(71) Applicant: Jing Liang, Rancho Palos Verdes, CA (US)

(72) Inventor: Jing Liang, Rancho Palos Verdes, CA (US)

( * ) Notice: Subject to any disclaimer, the term of this patent is extended or adjusted under 35 U.S.C. 154(b) by 0 days.

(21) Appl. No.: 18/464,967

(22) Filed: Sep. 11, 2023

(51) Int. Cl.
| | |
|---|---|
| *A61P 25/20* | (2006.01) |
| *A61K 36/258* | (2006.01) |
| *A61K 36/28* | (2006.01) |
| *A61K 36/72* | (2006.01) |
| *A61K 36/752* | (2006.01) |
| *A61K 36/882* | (2006.01) |

(52) U.S. Cl.
CPC ............ *A61K 36/72* (2013.01); *A61K 36/258* (2013.01); *A61K 36/28* (2013.01); *A61K 36/752* (2013.01); *A61K 36/882* (2013.01); *A61P 25/20* (2018.01)

(58) Field of Classification Search
CPC ...................................................... A61P 25/20
See application file for complete search history.

(56) References Cited

FOREIGN PATENT DOCUMENTS

CN 108721444 A * 11/2018

* cited by examiner

*Primary Examiner* — Qiuwen Mi
(74) *Attorney, Agent, or Firm* — Tsz Lung Yeung

(57) ABSTRACT

A herbal composition for relieving sleep disorder, comprising, by percentage weight, active ingredients of 2.5% *Hovenia* extract, 12.5% rattan extract, 7.5% lemon extract, 7.5% jujube kernels extract, 15% valerian root extract, and 5% *panax notoginseng*; auxiliary ingredients of 0.05% vitamin B1, 0.50% vitamin B3, 0.05% vitamin B6, 0.01% folic acid (vitamin B9), and 0.10% vitamin B12; and an accessory composition of 36.97% xylitol, 7.39% cellulose, 1.97% stearic acid, 0.99% natural color and flavor, 0.99% silicon dioxide, 0.49% croscarmellose Na, and 0.49% magnesium stearate. The herbal composition has significant anxiolytic effect, well-maintained bioavailability of DHM, no significant toxic or side effect and not causing addictive or withdrawal effect, thereby prolonging sleep duration and quality without causing any significant side effect.

13 Claims, 2 Drawing Sheets

COMPOSITION FOR RELIEVING SLEEP DISORDER AND ITS APPLICATION METHOD THEREOF

BACKGROUND OF THE PRESENT INVENTION

Field of Invention

The present invention relates to the field of Traditional Chinese Medicine, and more particularly to a method of using herbal remedies in oral form for treatment of or relieving sleep disorder.

Description of Related Arts

Trouble sleeping is a problem that afflicts many people. Statistically, 4 out of 10 people have insomnia. A good night's sleep has become a luxury. In order to sleep well, many people choose to take sleeping pills or supplements.

Prescription medications may include benzodiazepines, nonbenzodiazepines, antidepressants, and melatonin receptors, which may cause grogginess during the day and induce addiction. Most over-the-counter medicines have antihistamines, which may have common side effects of daytime sleepiness, dizziness, confusion, a decline in thinking skills, and trouble peeing. However, all these medications are not meant for long-term use. Sleeping pills can be very damaging to the body, and it is easy to develop tolerance and addiction.

Therefore, the development of a product, which has a high efficacy for sleep while is safe for human use with minimizes side effects without addiction, is urgently needed.

SUMMARY OF THE PRESENT INVENTION

An object of the present invention is to provide an herbal remedy for sleeping disorder which is non-additive, safe to use, and has long lasting effect.

Another object of the present invention is to provide an herbal composition to solve the problems of sleeping disorder, which is non-additive and has a high level of DHM bioavailability.

According to a preferred embodiment of the present invention, a composition for relieving sleep disorder, comprising:
  active ingredients, which includes: *Hovenia* extract, rattan extract, lemon extract, jujube kernels extract, valerian root extract, and *panax notoginseng*; and
  auxiliary ingredients, which includes: vitamin B1, vitamin B3, vitamin B6, folic acid (vitamin B9), and vitamin B12.

Preferably, the composition contains, by percentage weight, about 50% of active ingredients, about 1% of auxiliary ingredients.

Specifically, the composition contains, by percentage weight, 2.5% of *Hovenia* extract, 12.5% of rattan extract, 7.5% of lemon extract, 7.5% of jujube kernels extract, 15% of valerian root extract, 5% of *panax notoginseng*; 0.05% of vitamin B1, 0.50% of vitamin B3, 0.05% of vitamin B6, 0.01% of folic acid (vitamin B9), and 0.10% of vitamin B12.

Preferably, the lemon extract is a blended mixture of a whole fruit of lemon, including the outer skin and everything enclosed by the outer skin.

Preferably, the composition contains an accessory composition comprising: xylitol, cellulose, stearic acid, natural color and flavor, silicon dioxide, croscarmellose Na, and magnesium stearate. The composition contains about 49% of accessory composition.

In particular, the accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate.

The composition is prepared into one 2 g serving size in a jelly form, a powder form, a tablet form or a liquid form.

Preferably, the composition is prepared into one 2 g serving size in oral administration form and a dosage of the composition is 2 g/kg daily for three months.

The composition can achieve comparable anxiolytic effect comparable to diazepam while not having any significant side effect. The composition also can improve sleep quality without causing any addiction effect within a short period of time, and is more effective than melatonin without causing any significant side effect.

The composition of the present invention can maintain DHM bioavailability, increase its efficacy, and improve the quality of sleep. The composition also has significant anxiolytic effects, similar to the dosage of diazepam to induce anxiolytic effects. The composition, unlike benzodiazepines (BZs), does NOT induce dependence or addiction, which is very important for developing a sleep aid formula. The composition does not have any negative records of safety or toxicity. All the individual active ingredients have been used historically for more than 500 years. The composition not only has the effect of promoting good sleep and relaxation, but also has other health benefits, such as memory and cognition improvements, and reducing anxiety.

DETAILED DESCRIPTION OF THE PREFERRED EMBODIMENT

Figure 1:
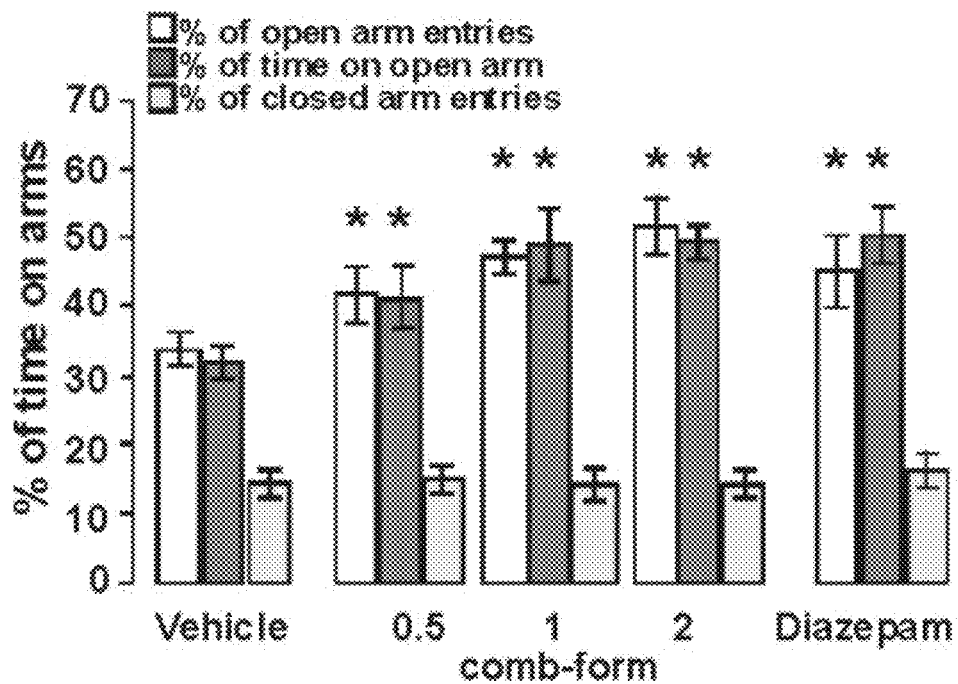
FIG. 1 illustrates an anxiolytic effect of a herbal composition according to a preferred embodiment of the present invention.

Herbal remedies are consumed by approximately 50% of the population in the US for health and wellness, including products promoted for sleep problems and mental health issues.

Dihydromyricetin (DHM) is an anti-alcohol intoxication medication. Dihydromyricetin (DHM, 1 mg/kg, i.p. injection) can counteract acute alcohol (EtOH) intoxication, and also withdrawal signs in rats including tolerance, increased anxiety and seizure susceptibility. DHM greatly reduced EtOH consumption in an intermittent voluntary EtOH intake paradigm in rats. At the cellular levels, DHM (1 μM) antagonized both acute EtOH-induced potentiation of $GABA_ARs$ and EtOH exposure/withdrawal-induced $GABA_AR$ plasticity, including alterations in responsiveness of extra- and post-synaptic $GABA_ARs$ to acute EtOH, and most importantly, increases in $GABA_AR$ α4 subunit expression in hippocampus and cultured neurons. DHM has been used as a hangover remedy and is an over-the-counter herbal remedy, which can help the body metabolize alcohol faster and treat alcohol use disorders. In particular, DHM has been used for easing headaches and providing protection to the liver. DHM has been used in Asia for thousands of years as a hangover cure and anti-intoxication medicine and is considered safe for humans even in massive doses.

According to the present invention, Dihydromyricetin (DHM), a bioflavonoid extracted from *Hovenia* or Rattan tea (vine), can counteract anxiety and depression via $GABA_A$ receptor ($GABA_AR$) activity. DHM can counteract EtOH intoxication and withdrawal via $GABA_AR$ activity. The activity of DHM is unique through combination with other remedies, such as resveratrol extracted from grape seed, genistein extracted from soy bean, daidzein extracted from Kudzu, and turmeric extracted from the ginger family. The levels of $GABA_AR$ potentiation are different based on the different combinations with DHM.

DHM is a positive modulator of $GABA_AR$ and the role of $GABA_AR$ is to initiate sleep. Therefore DHM can be used to affect the levels of $GABA_AR$ to relieve sleep disorder, and is a major ingredient used in the sleep aid supplement according to the preferred embodiment of the present invention.

According to the preferred embodiment of the present invention, DHM is the core ingredients, and other active ingredients and auxiliary ingredients are also added to DHM so as to increase its effects to relieve sleep disorders.

According to a preferred embodiment of the present invention, a composition for relieving sleep disorder, comprising:
  active ingredients comprising: *Hovenia* extract, rattan extract, lemon extract, jujube kernels extract, valerian root extract, and *panax notoginseng*;
  auxiliary ingredients comprising: vitamin B1, vitamin B3, vitamin B6, folic acid (vitamin B9), and vitamin B12; and
  an accessory composition comprising: xylitol, cellulose, stearic acid, natural color and flavor, silicon dioxide, croscarmellose Na, and magnesium stearate.

The composition contains, by percentage weight, about 50% of active ingredients, about 1% of auxiliary ingredients and about 49% accessory composition.

*Hovenia* or Rattan tea (vine) contains high component of dihydromyricetin (DHM), a bioflavonoid which can counteract anxiety and depression via $GAB_AA$ receptor ($GABA_AR$) activity.

*Hovenia* extract refers to the extract prepared by seed of *Hovenia dulcis Thunberg*. Rattan extract refer to the extract prepared by the leaf of Rattan.

Lemon, Lisbon Lemons, contains flavonoids, natural compounds with antioxidant and anti-inflammatory properties. Major types of flavonoids found in lemon include hesperidin, quercetin (similar to DHM), rutin, naringin, and eriocitrin. Flavonoids in lemon are associated with potential benefits such as antioxidant protection, heart health support, anti-inflammatory effects, and immune system support.

It is worth mentioning that, according to the preferred embodiment of the present invention, the lemon extract is a blended mixture of the whole lemon fruit (Lisbon Lemons), including the outer skin and all the fruit and seeds inside. The lemon extract can greatly increase the bioavailability of the active ingredients of the composition of the present invention.

Figure 3:
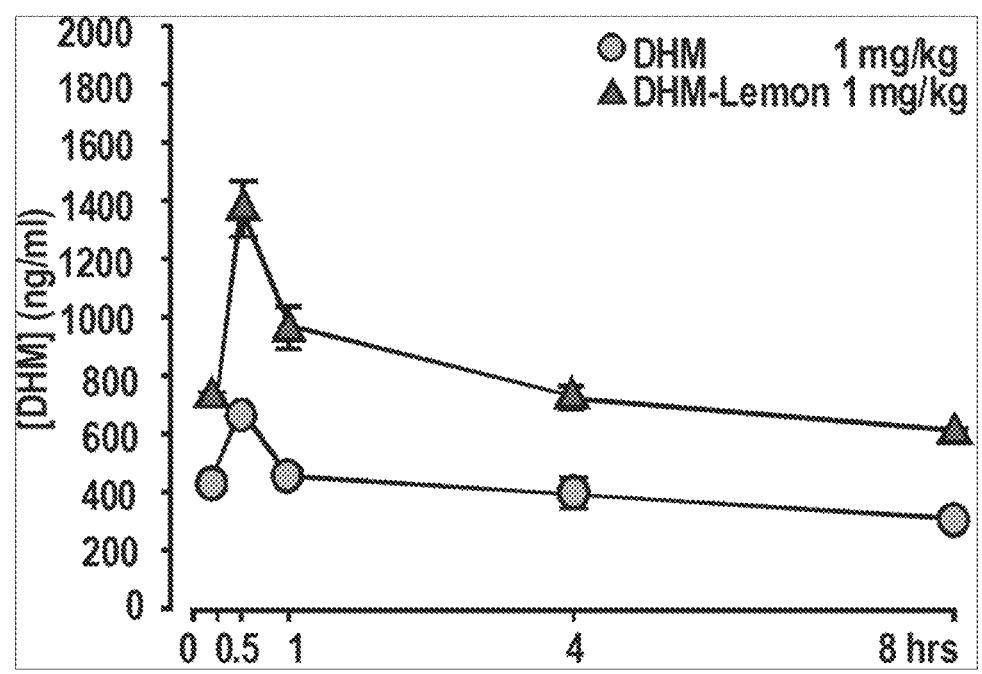
FIG. 3 illustrates the results of DHM bioavailability of DHM with or without lemon extract according to the present invention.

DHM absorption with or without lemon extract is studied by using DHM (300 mg DHM) and DHM-lemon (300 mg DHM and 150 mg lemon extract). The results show that the specific lemon extract of the present invention can dramatically increase DHM bioavailability and absorption, which is shown in FIG. 3 of the drawings.

In general, after DHM is orally administered, the DHM will go through the gastrointestinal tract and the bioavailability will decrease dramatically to about 4% or lower. So, the effect of orally administered DHM in improving the sleeping quality cannot be observed, or cannot be significantly or sufficiently observed. However, with the addition of lemon extract of the present invention, the bioavailability can be dramatically increased to about 40%. In other words, the combination effect of DHM and the lemon extract in the specific form and ratio of the present invention can show a very strong, unexpected and effective result in improving the sleep quality.

Jujube kernel extract, which is derived from the seed of jujube kernels, is an essential component for calming the nerves in traditional Chinese medicine. As a sedative, Jujube kernels have two types of phytochemicals; saponins and flavonoids, which trigger changes to neurotransmitters, including GABA and serotonin, which can make it easier to fall asleep and stay asleep. At least one of the saponins in jujube, jujuboside A, helps to quiet activity in the hippocampus region of the brain. And jujube contains a flavonoid compound, spinosin, which appears to trigger sleepiness through its effects on serotonin.

Valerian root extract is a concentrated form of the valerian plant's medicinal properties. Valerian root extract is used as a natural remedy to reduce anxiety and improve sleep quality. The extract contains compounds that promote relaxation by potentially increasing GABA levels and calming the nervous system, but may also cause drowsiness and other side effects.

*Panax Notoginseng*, root of *Panax Notoginseng*, is a traditional Chinese medicine used to assist with sleep difficulties and support healthy sleeping patterns. It works by reducing restlessness during sleep, increasing and improving sleep time and duration.

Vitamin B1 can maintain the normal function of the nervous system and help the body's mood to calm down. Vitamin B3, also called niacin or niacinamide, plays an important role in the metabolism of the central nervous system. Vitamin B6 plays a key role in the synthesis of serotonin, and serotonin (also called serotonin). Folic acid (Vitamin B9) is distributed in cerebrospinal fluid and extracellular fluid and can relieve depression. Vitamin B12 helps reduce the symptoms of neurological and mental diseases such as depression, insomnia, and mild memory loss.

Preferably, in a 2 g serving size formula, and the composition contains, by percentage weight, 50% of active ingredients, 0.71% of auxiliary ingredients and 49.49% accessory composition.

In particular, the active ingredients contain, by percentage weight, 2.5% of *Hovenia* extract, 12.5% of rattan extract, 7.5% of lemon extract, 7.5% of jujube kernels extract, 15% of valerian root extract, and 5% of *panax notoginseng*; the auxiliary ingredients contain, by percentage weight, 0.05% of vitamin B1, 0.50% of vitamin B3, 0.05% of vitamin B6, 0.01% of folic acid (vitamin B9), and 0.10% of vitamin B12; and the accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate.

The composition may be prepared into one 2 g serving size in a jelly form, a powder form, a tablet form or a liquid form, for oral administration.

It is worth mentioning that since the different active ingredients are used as herbs or groceries for more than hundreds year, and there's no report of side effect report based on literature search, all the active ingredients are safe to use without any significant side effect.

Experiment 1: Study of Characteristic of the Anxiolytic Effects of Comb-Form (0.5, 1, and 2) by Elevated Plus Maze EPM Test The effects of the composition according to the preferred embodiment of the present invention at 0.5, 1, and 2 serving size on the behavior of mice in EPM test is studied.

Control and diazepam groups are used for comparison.

Testing Compositions:

The composition for relieving sleep disorder bases on Traditional Chinese Medicine according to the preferred embodiment of the present invention is prepared into one 2 g serving size containing 50 mg Hovenia extract, 250 mg rattan extract, 150 mg lemon extract, 150 mg jujube kernels extract, 300 mg valerian root extract, 100 mg panax notoginseng; 1 mg vitamin B1, 10 mg vitamin B3, 1 mg vitamin B6, 0.2 mg folic acid (vitamin B9), 2 mg vitamin B12, and 49.29% by percentage weight of accessory composition. The accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate. The composition is further prepared into a 0.5 g, 1 g and 2 g serving sizes to study the effect of the composition at different dosages (serving sizes). The composition at 0.5 g, 1 g and 2 g serving sizes are denoted by comb-form 0.5, comb-form 1 and comb-form 2 respectively.

The vehicle refers to a composition containing the accessory composition only, without the active ingredients and the auxiliary ingredients. The vehicle serves as a composition for the control group.

Diazepam refers to a composition containing active ingredient of diazepam only. The diazepam serves as a composition for the comparison group.

In each of the five groups, 7 mice are used in one group and a total of 35 mice are used.

Methodology:

Elevated plus maze (EPM) test for mice consists of two opposing open (24×8 cm) and two enclosed arms (24×8×25 cm) connected by a central platform forming the shape of a plus sign. The dimensions of the central field which connects the open and closed arms are 8×8 cm. The plus maze is elevated to a height of 50 cm. Each mouse is immediately placed in the central square of the apparatus with the head facing one of the closed arms. Mice behavior during 5 min is observed and recorded by means of a video camera (Canon Digital, Japan), which is fixed to the wall above the elevated plus maze. In this test, the following parameters are detected and calculated: the number of entries (open arm entries and closed arm entries), % of open arm entries, and % of time spent in open arms.

The EPM is an etiologically valid assessment of anxiolytic/anxiety in rodents because it uses natural stimuli (fear of a novel, brightly-lit open space, and fear of balancing on a relatively narrow, raised platform) to determine anxiety-like behavior in animals. Anxiolytics are known to exert their pharmacological action by causing an increase in GABAergic neurotransmission in the brain. EPM is routinely used for the evaluation of anxiolytic activity of substances in rodent models. $GABA_A Rs$ are involved in the anxiolytics effects of benzodiazepines.

Data is expressed as the means (±SEM, n=7/group) percentage of open arm entries or of time spent on open arms, and the number of closed arm entries in mice given a 5-min test, 45 minutes after oral administration of the testing compositions.

Statistical analysis: one-way ANOVA, followed by Holm-Sidak post hoc comparison is used for control (vehicle) versus treatment (comb-form or diazepam) groups, *: $p<0.01$.

Results:

Referring to FIG. 1 of the drawings, the anxiolytic effect of comb-form 0.5, comb-form 1 and comb-form 2 evaluated by Elevated Plus Maze EPM test is illustrated.

In EPM test, both comb and diazepam significantly altered the total number of arm entries with little effect in the number of closed arm entries (as shown in FIG. 1). Analysis showed that diazepam (2 mg/kg) and comb-form (0.5, 1, 2 g serving size) can significantly increase the total number of arm entries, and significantly elevate the percentage of open arm entries ($p<0.01$) dosage-dependently. The data indicates that the comb-form has significant anxiolytic effects, similar to the dosage of diazepam to induce anxiolytic effects.

In other words, all of the comb-form 0.5, comb-form 1 and comb-form 2 can exert significant anxiolytic effects in EPM test.

CONCLUSION

The comb-form can elicit anxiolysis, as observed in the selective increase in the number of entries and time spent on open arms.

The dose-dependent increases in both the number of open arms entries and time on open arms are detected after oral administration of comb-form, and responses are roughly equivalent to diazepam (2 mg/kg, a typical anxiolytic dosage).

The comb-form 0.5, comb-form 1 and comb-form 2 have significant stress-alleviating effects.

Experiment 2: Sleep Quality and Addiction Effect of Comb-Form (0.5, 1, and 2)

The Anecdotal Test of the effects of the composition according to the preferred embodiment of the present invention at 2 g serving size on sleep is studied. DHM and Melatonin groups are used for comparison.

Testing Compositions:

The composition for relieving sleep disorder bases on Traditional Chinese Medicine according to the preferred embodiment of the present invention is prepared into one 2 g serving size containing 50 mg Hovenia extract, 250 mg rattan extract, 150 mg lemon extract, 150 mg jujube kernels extract, 300 mg valerian root extract, 100 mg panax notoginseng; 1 mg vitamin B1, 10 mg vitamin B3, 1 mg vitamin B6, 0.2 mg folic acid (vitamin B9), 2 mg vitamin B12, and 49.29% by percentage weight of accessory composition. The accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate. The composition at 2 g serving size is denoted by comb-DHM.

DHM refers to a composition containing 250 mg of DHM only. Melatonin refers to a composition containing only 10 mg of melatonin.

Testing Groups:

The comb-DHM group receives one 2 g serving size of comb-DHM. The DHM group received 250 mg of DHM. The Melatonin group receives 10 mg of melatonin. The comb-DHM, DHM, and melatonin are taken orally daily.

In each group, there are 200 testing subjects.

Methodology:

More than 60% of testing subjects are experienced melatonin users. The testing subjects have severe sleep problems. Their average sleep duration is about 2.5 hours per night. The testing subjects are given oral forms of comb-DHM (one 2 g serving size), DHM (250 mg), or melatonin (10 mg) once a day for three months. After one week, data of their reported sleep duration is collected. The testing subjects have an average body weight of 70 kg. After the course of three months, the testing subjects are followed up for another three months without taking any testing compositions.

Figure 2:
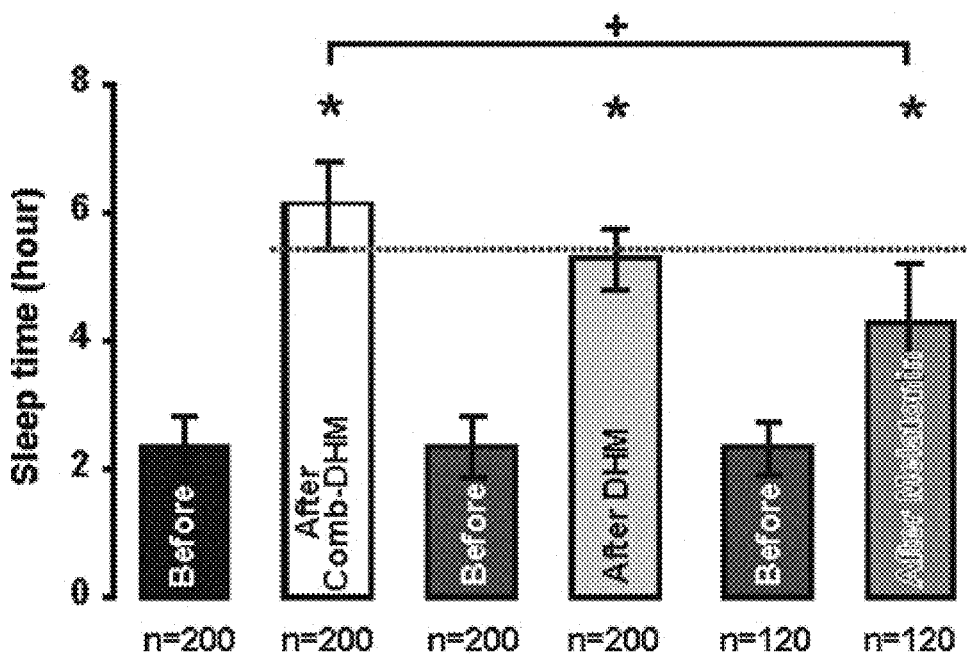
FIG. 2 illustrates the results of Anecdotal Test of the herbal composition according to the above preferred embodiment of the present invention.

Results:

Referring to FIG. 2 of the drawings, the Comb-DHM group, after taking Comb-DHM, have improved sleep duration, from an average of 2.4±0.65 hours to an average of 6.5±0.75 hours. The DHM group have improved sleep duration, for an average of 5.5±0.65 hours. Comb-DHM and DHM groups have reported improved sleep symptoms starting between 1-7 days. Melatonin has improved sleep duration to an average of 4.3±0.9 hours in 40% attendees, but the improved sleep symptoms start after a month. Only the melatonin group complain of dizziness, loss of energy, and other feelings of discomfort on the second day.

After finishing the three-month tests, the testing subjects are followed up for another three months. The comb-DHM and DHM groups continue having good sleep quality everyday without dependence. But the melatonin group suffer withdrawal from the test, and most participants have asked for melatonin to maintain good sleep quality, indicating an addiction trend or melatonin dependence.

It is also observed in this Experiment 2 that using only DHM to induce participates to sleep will take longer time to see the effects while using comb-DHM will quickly see the improvement of sleep.

The data indicates that the effect of promoting sleep and improving the quality of sleep by taking the comb-DHM has been agreed upon by many users. The comb-DHM is an effective formula with scientific data support.

In conclusion, the comb-DHM can improve the quality of sleep without addiction.

It is worth mentioning that the composition of the present invention has a clear mechanism of action and target. The anxiolytic effects have been identified. The different active ingredients of the composition of the present invention are listed in the Compendium of *Materia Medica* and have been used in the Eastern clinical field for more than 500 years without any negative records of usages. The specific formula of the present invention is an effective combination formula with support from scientific data and the Compendium of *Materia Medica*. In conclusion, the present invention combines the research achievements on DHM and traditional Chinese medicine and clinical practice, resulting in a combinatorial formula that could significantly improve the quality of sleep. The resulting combination formula provides an alternative treatment to alleviate pain from sleep disorders.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A herbal composition for relieving sleep disorder, comprising:
   active ingredients of *Hovenia* extract, rattan extract, lemon extract, jujube kernels extract, valerian root extract, and *panax notoginseng*; and
   auxiliary ingredients of vitamin B1, vitamin B3, vitamin B6, folic acid, and vitamin B12,
   wherein the herbal composition has a ratio of a sum of *Hovenia* extract and rattan extract to lemon extract of 2:1 by percentage weight, thereby providing a dihydromyricetin bioavailability of 40%, the herbal composition has significant anxiolytic effect and increases a sleep duration of a human subject.

2. The herbal composition according to claim 1, wherein the herbal composition is in an oral administration form selected from the group consisting of a jelly form, a powder form, a tablet form, a capsule form and a liquid solution form.

3. The herbal composition according to claim 2, wherein the lemon extract is a blended mixture of a whole fruit of lemon, including an outer skin and everything enclosed by the outer skin.

4. The herbal composition according to claim 3, further comprising an accessory composition of: xylitol, cellulose, stearic acid, natural color and flavor, silicon dioxide, croscarmellose Na, and magnesium stearate.

5. The herbal composition according to claim 1, the composition contains, by percentage weight, 2.5% of *Hovenia* extract, 12.5% of rattan extract, 7.5% of lemon extract, 7.5% of jujube kernels extract, 15% of valerian root extract, 5% of *panax notoginseng*; 0.05% of vitamin B1, 0.50% of vitamin B3, 0.05% of B vitamin B6, 0.01% of folic acid, and 0.10% of vitamin B12.

6. The herbal composition according to claim 4, the composition contains, by percentage weight, 2.5% of *Hovenia* extract, 12.5% of rattan extract, 7.5% of lemon extract, 7.5% of jujube kernels extract, 15% of valerian root extract, 5% of *panax notoginseng*; 0.05% of vitamin B1, 0.50% of vitamin B3, 0.05% of vitamin B6, 0.01% of folic acid, and 0.10% of vitamin B12.

7. A herbal composition for relieving sleep disorder, comprising: active ingredients of *Hovenia* extract, rattan extract, and lemon extract, wherein a ratio of a sum of *Hovenia* extract and rattan extract to lemon extract is 2:1 by percentage weight and the lemon extract is a blended mixture of a whole fruit of lemon, including an outer skin and everything enclosed by the outer skin, wherein the herbal composition is prepared into a tablet form, a capsule form or a jelly form.

8. The herbal composition according to claim 7, wherein the herbal composition has a dihydromyricetin bioavailability of 40%.

9. The herbal composition according to claim 8, wherein a weight of the *Hovenia* extract and the rattan extract combined is 300 mg and a weight of lemon extract is 150 mg, wherein the herbal composition is for a user having a body weight of about 70 kg, wherein the herbal composition is prepared into the jelly form.

10. The herbal composition according to claim 8, further comprising an accessory composition of: xylitol, cellulose, stearic acid, natural color and flavor, silicon dioxide, croscarmellose Na, and magnesium stearate.

11. The herbal composition according to claim 8, the composition contains, by percentage weight, 2.5% of *Hov-*

*enia* extract, 12.5% of rattan extract, 7.5% of lemon extract, 7.5% of jujube kernels extract, 15% of valerian root extract, 5% of *panax notoginseng;* 0.05% of vitamin B1, 0.50% of vitamin B3, 0.05% of B vitamin B6, 0.01% of folic acid, and 0.10% of vitamin B12.

12. The herbal composition according to claim 4, wherein the accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate, wherein the herbal composition has significant anxiolytic effect and increases a sleep duration of a human subject without any significant side effect.

13. The herbal composition according to claim 10, wherein the accessory composition contains, by percentage weight, 36.97% of xylitol, 7.39% of cellulose, 1.97% of stearic acid, 0.99% of natural color and flavor, 0.99% of silicon dioxide, 0.49% of croscarmellose Na, and 0.49% of magnesium stearate, wherein the herbal composition has significant anxiolytic effect and increases a sleep duration of a human subject without any significant side effect.

\* \* \* \* \*